(12) United States Patent
Subramanian et al.

(10) Patent No.: US 7,034,930 B1
(45) Date of Patent: Apr. 25, 2006

(54) SYSTEM AND METHOD FOR DEFECT IDENTIFICATION AND LOCATION USING AN OPTICAL INDICIA DEVICE

(75) Inventors: Ramkumar Subramanian, San Jose, CA (US); Khoi A. Phan, San Jose, CA (US); Bharath Rangarajan, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 1442 days.

(21) Appl. No.: 09/634,302

(22) Filed: Aug. 8, 2000

(51) Int. Cl.
*G01N 21/88* (2006.01)
(52) U.S. Cl. .................... 356/237.2; 356/397
(58) Field of Classification Search ................ 356/614, 356/615, 616, 617, 237.2, 237.3, 237.4, 237.5, 356/390, 397
See application file for complete search history.

(56) References Cited

U.S. PATENT DOCUMENTS

| | | | |
|---|---|---|---|
| 4,183,614 A | 1/1980 | Feldman | |
| 4,185,298 A * | 1/1980 | Billet et al. | 356/390 |
| 4,544,244 A | 10/1985 | Moore | |
| 4,633,504 A * | 12/1986 | Wihl | 356/237.5 |
| 5,218,195 A | 6/1993 | Hakamata | |
| 5,644,399 A * | 7/1997 | Hoshiyama | 356/397 |
| 6,002,136 A | 12/1999 | Naeem | |
| 6,067,154 A * | 5/2000 | Hossain et al. | 356/237.2 |

* cited by examiner

*Primary Examiner*—Richard A. Rosenberger
(74) *Attorney, Agent, or Firm*—Eschweiler & Associates, LLC

(57) ABSTRACT

A measuring system and method are provided for defect identification and location. The system an optical measurement device adapted to view a workpiece along an optical path, and an optical indicia device located in the optical path between the workpiece and the measurement device, which is adapted to provide location information to the system or a user. The location information can be used to correlate defect locations identified in a wafer before and after a process step, as well as between two different wafers. The optical indicia device may further allow the use of field comparison techniques in identifying and locating defects in a blank or unpatterned workpiece. The indicia device may comprise, for example, a transparent member having a grid or other optical indicia patterned thereon, allowing inspection of the workpiece with reference to the optical indicia pattern.

13 Claims, 13 Drawing Sheets

40a

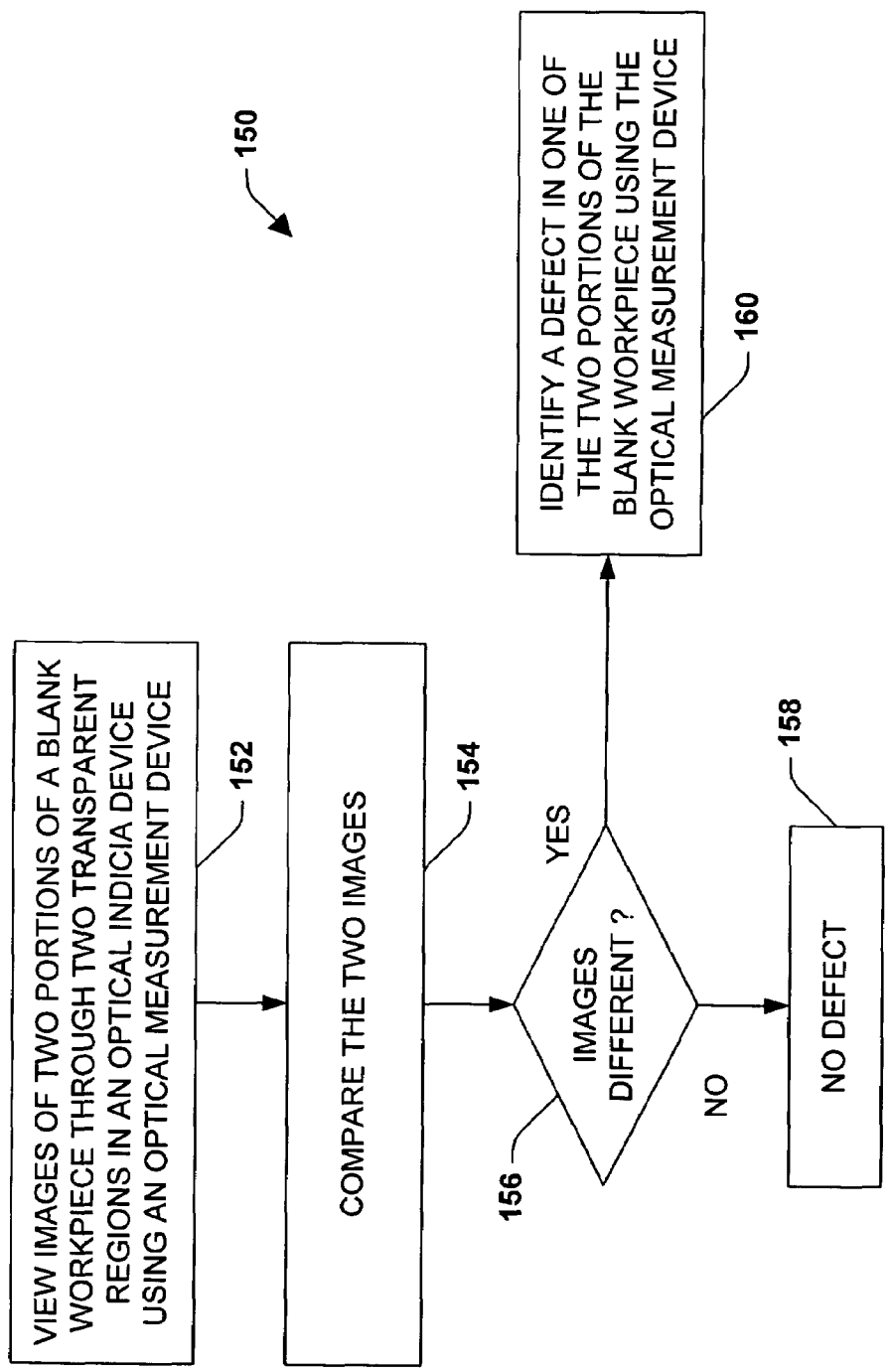

SYSTEM AND METHOD FOR DEFECT IDENTIFICATION AND LOCATION USING AN OPTICAL INDICIA DEVICE

The present invention relates generally to measurement instruments used to analyze defects in a semiconductor workpiece, and more particularly to a system and method for optically identifying and locating defects in a semiconductor wafer or other type of workpiece using an optical indicia device.

BACKGROUND OF THE INVENTION

In the semiconductor industry there is a continuing trend toward higher device densities. To achieve these high densities there have been, and continue to be, efforts toward scaling down the device dimensions on semiconductor wafers. In order to accomplish such a high device packing density, smaller features sizes are required. This may include the width and spacing of interconnecting lines and the surface geometry such as the corners and edges of various features.

The requirement of small features with close spacing between adjacent features requires high resolution photo lithographic processes as well as high resolution inspection instruments. In general, lithography refers to processes for pattern transfer between various media. It is a technique used for integrated circuit fabrication in which, for example, a silicon wafer is coated uniformly with a radiation-sensitive film (e.g., a photoresist), and an exposing source (such as ultraviolet light, x-rays, or an electron beam) illuminates selected areas of the film surface through an intervening master template (e.g., a mask or reticle) to generate a particular pattern. The exposed pattern on the photoresist film is then developed with a solvent called a developer which makes the exposed pattern either soluble or insoluble depending on the type of photoresist (i.e., positive or negative resist). The soluble portions of the resist are then removed, thus leaving a photoresist mask corresponding to the desired pattern on the silicon wafer for further processing.

The trend toward higher device densities in the manufacture of semiconductor devices also requires higher resolution scanning and inspection instruments for analyzing various features of semiconductor devices. A measuring apparatus is required to inspect semiconductor devices in association with manufacturing production line quality control applications as well as with product research and development. The ability to scan and/or view particular features in a semiconductor workpiece allows for adjustment of manufacturing processes and design modifications in order to produce better products, reduce defects, etc. Accordingly, various inspection tools, such as those commercially available from KLA-Tencor, Orbot, and Inspex, have been developed to map and record wafer surface features and defects.

Defects may occur at various steps in the process of manufacturing a semiconductor product. In the development and testing of new semiconductor processing methods, it is desirable to determine which step or steps in the process are causing defects. Defect detection is also important in identifying tool cleanliness problems and trends. For example, when a silicon wafer is coated with a radiation-sensitive film or photoresist in a wafer track, particulate matter may be deposited on the wafer due to an unclean coating environment. In addition to particle defects, chemical defects are problematic and may be caused by improper ingredients or mixture ratios in the photoresist. The interaction of such chemically defective photoresist with the wafer may leave a residue on the coated wafer surface which may be detected using optical inspection tools. In similar fashion, the photoresist development process may also introduce defects into a wafer. These may include particle as well as chemistry defects.

Defects in a semiconductor wafer may be spatially repeatable. For example, a pattern defect may be caused by a mark or blemish in the mask used in a patterning step. This may cause a defect that is locationally repeatable, whereby the defect may occur at the same location in wafers patterned using the blemished mask. Similarly, dirt or marks on an exposing tool lens may cause such locationally repeatable defects in a plurality of wafers processed by the tool. Other defects may be regionally repeatable. For example, a photoresist deposition step may be performed while a wafer is rotated. Defects occurring in such a processing step may be radially repeatable, whereby defects occur according to a probability distribution in a region radially spaced from the center of the wafer by a certain distance or range. Thus, although individual defects in individual wafers may be somewhat randomly located in such a region, the region in which such defects occur may be repeatable.

Where a semiconductor wafer has been processed according to a multi-step procedure, it is desirable to identify defects associated with individual processing steps, in order to make appropriate corrections and adjustments to the process and/or to specific processing tools. Particle defects, as well as chemical residue defects may be identified in a wafer using optical measuring instrumentation and systems, such as optical microscopes. However, it may be difficult to determine the process step at which a particular defect, whether particulate or chemical, was introduced based on inspection of a single wafer. For example, a particle defect may be introduced in a photoresist deposition step in a wafer track. Thereafter, the wafer may be patterned using an exposing source via a mask or reticle. The patterned wafer is then coated with a developer solvent to make the exposed pattern either soluble or insoluble according to the type of photoresist employed. The wafer may be optically inspected after the soluble portions of the photoresist have been removed, whereby a defect may be identified. However, without prior inspection of the wafer or other quantization of the defects associated with the initial processing steps, it may be difficult to determine the step at which a defect occurred.

Optical inspection of patterned wafers is typically done using field comparison techniques. The patterning of such wafers commonly includes many fields having theoretically identical component patterns therein. For example, each such field may include a processor or other device. Field comparison techniques presume that where one field in such a patterned wafer is different from the rest of the fields, a significant probability exists that a defect exists in that field. This technique is employed by inspection tools and personnel in quickly identifying likely defects in a patterned wafer.

Although a defect caused in one step (e.g., a photoresist deposition step) may be detectable after multi-step processing, such a defect may be difficult or impossible to differentiate from a defect introduced at a later step, based on a single inspection of the wafer. In characterizing a particular semiconductor processing method, it is desirable to detect a defect in a wafer, and further to identify the process step at which the defect occurred. Accordingly, there remains a need for improved systems and methodologies by which defects in processed wafers, may be identified and located, and by which the causes thereof may be determined. Defect inspections may occur in a blank or unpatterned wafer following an initial processing step, such as a photoresist deposition step. Since the blank wafer has not been patterned, there are no fields. Consequently, field comparison techniques cannot be easily employed to determine the location of defects identified in a blank wafer. Thus, there remains a need for improved systems and methodologies by which defects in a blank wafer may be more easily identified.

SUMMARY OF THE INVENTION

A measuring system and method are provided which overcome or minimize the problems and shortcomings of conventional defect identification systems. The invention includes an optical defect inspection system having an optical measurement device adapted to view a workpiece along an optical path, and an optical indicia device in the optical path, adapted to provide location information to the system or a user. The location information can be used to correlate defect locations identified in a wafer before and after a process step, as well as between two different wafers. In addition, the optical indicia device may further allow the use of field comparison techniques in identifying and locating defects in a blank or unpatterned workpiece, by providing fields in a blank workpiece, which may advantageously be compared by the optical measurement device.

The indicia device may comprise, for example, a transparent member having a grid or other optical indicia patterned thereon. The workpiece surface may be selectively exposed to the optical measurement device (e.g., an optical microscope) through one or more regions in the transparent member, whereby a coordinate system is provided for quantifying the location of the workpiece being viewed at a given time. The inspection system thus allows a user to easily locate a specific area or region of the workpiece for viewing and other analysis. This system may be advantageously employed in comparing patterned and unpatterned or blank semiconductor wafer workpieces, to determine at which processing step a particular defect occurred. The invention further provides methods of detecting and locating defects in patterned and unpatterned workpieces, whereby an optical indicia device is used to identify and locate defects in a blank workpiece, and to correlate the blank workpiece defects with defects identified in a patterned workpiece. The optical indicia device may further be employed in identifying defects in a blank wafer, to facilitate the use of field comparison techniques to quickly locate defects.

In accordance with one aspect of the invention, there is provided an optical defect inspection system for identifying and locating defects in a workpiece, comprising an optical measurement device adapted to view the workpiece along an optical path, and an optical indicia device located in the optical path, adapted to provide location information to the system or a user. The optical indicia device may comprise, for example, a transparent member having non-transparent optical indicia (e.g., lines) thereon defining a plurality of transparent fields or regions. This provides a grid or other pattern used for determining the location of one or more features on a workpiece, such as particulate or chemical residue defects. The optical indicia device may be moveable in one or more axis relative to the workpiece and/or the optical microscope, to thereby provide for coarse and fine defect location operation. The optical indicia device may further be adapted to move in and out of the optical path of the microscope, to further facilitate defect identification and location.

According to another aspect of the invention, a method of identifying and locating defects in a workpiece is provided. The method may be implemented in an optical defect inspection system having an optical measurement device adapted to view a workpiece along an optical path and an optical indicia device located in the optical path between the workpiece and the optical measurement device. The method includes identifying a first defect in a first workpiece (e.g., a patterned workpiece) using the optical measurement device and determining the location of the first defect using the optical indicia device.

A defect may be identified in a patterned wafer, for example, using field comparison techniques, wherein the inspection tool may programmatically perform an optical comparison of one or more theoretically identical pattern features on the wafer. The optical indicia device (e.g., a grid) may then be moved into the optical path to provide location information relating to the location of the defect in the patterned wafer. The method further includes inspecting a portion of a second workpiece (e.g., a blank workpiece) using the optical measurement device and the optical indicia device according to the location of the first defect in the first workpiece. Thus, a blank wafer may be inspected at a location corresponding to the defect location in the patterned wafer.

The method further includes determining whether a second defect exists in the portion of the second workpiece using the optical measurement device, and if so, correlating the first and second defects according to the location of the first defect in the first workpiece. Such a correlation may account for regionally as well as locationally repeatable workpiece defects. For instance, if a defect exists in the same or related locations on a blank wafer and a patterned wafer, it may be possible to determine that the error in the patterned wafer occurred prior to the patterning step in the manufacturing process. The method thus provides for determination of process steps causing defects, as well as the elimination of certain process steps as potential causes of specific defects, through the correlation.

According to yet another aspect of the invention, another method of identifying and locating defects in the workpiece is provided. The method includes identifying a blank workpiece defect in a blank workpiece using the optical measurement device, determining the location of the blank workpiece defect using the optical indicia device, identifying a patterned workpiece defect in a patterned workpiece using the optical measurement device, determining the location of the patterned workpiece defect using the optical indicia device, and correlating the locations of the blank workpiece defect and the patterned workpiece defect in order to determine the cause of the patterned workpiece defect. By this method, the defects in two or more wafers may be mapped, whereby a correlation of the defect maps may provide information as to the particular step or steps in a manufacturing process at which defects are occurring.

According to still another aspect of the invention, an optical indicia device is provided for use in an optical defect inspection system. The device includes a planar transparent member having non-transparent optical indicia defining a plurality of transparent regions in the transparent member along an axis perpendicular to the plane of the transparent member. The plurality of transparent regions have a shape associated therewith, which may be rectangular or hexagonal. For example, the non-transparent optical indicia may be lines in some pattern to provide a coordinate system or spacial reference to indicate the location of a particular workpiece feature being inspected.

According to another aspect of the invention, there is provided a method for identifying a defect in a blank workpiece in an optical defect inspection system having an optical measurement device adapted to view a workpiece along an optical path and an optical indicia device located in the optical path between the workpiece and the optical measurement device and having a transparent member with non-transparent optical indicia defining a plurality of transparent regions in the optical indicia device along the optical path. The method includes viewing the images of two portions of the workpiece through two of the transparent regions using the optical measurement device, comparing the images of the two portions of the workpiece, and identifying a defect in the workpiece in one of the two portions of the workpiece if there is a difference in the images of the two portions of the workpiece. The method thus allows the use of field comparison techniques to facilitate quick identification of defects in a blank wafer.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 9 is a flow diagram illustrating an exemplary method of identifying a defect in a blank workpiece according to another aspect of the invention.

DETAILED DESCRIPTION OF THE INVENTION

Figure 1:
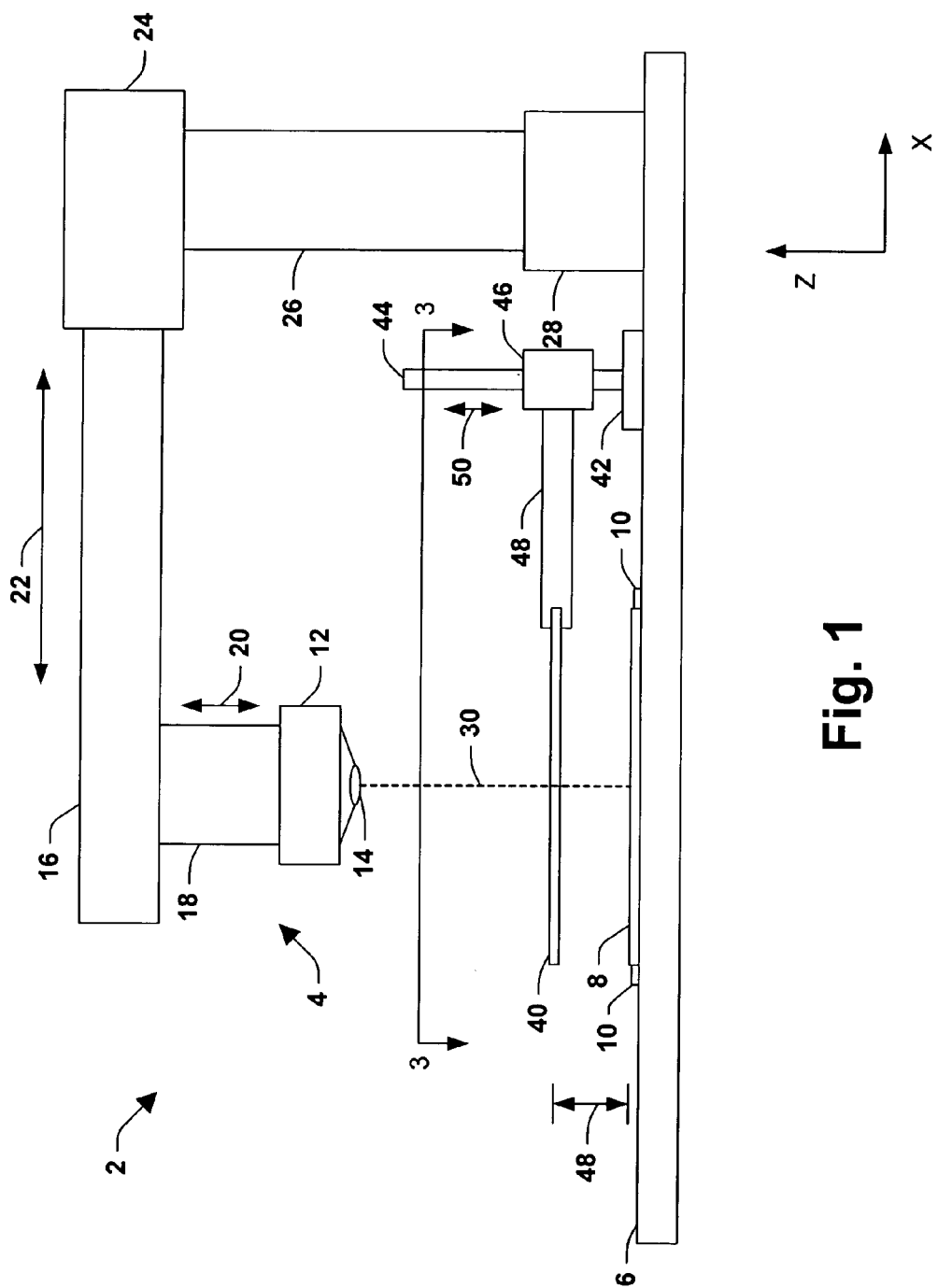
FIG. 1 is a side elevation view of an exemplary optical defect inspection system including an optical indicia device in accordance with an aspect of the present invention.

The following is a detailed description of the present invention made in conjunction with the attached figures, wherein like reference numerals will refer to like elements throughout. The invention provides a system and methods by which workpiece defects and their causes may be identified and located. The invention finds particular application in the field of semiconductor manufacturing. However, it will be recognized that other applications are possible within the scope of the invention. In particular, the various aspects of the invention may be employed to determine which step in a multi-step semiconductor manufacturing process is causing defects in a semiconductor wafer.

Referring to FIG. 1, an exemplary optical defect inspection system 2 is illustrated having an optical measurement device (e.g., an optical microscope) 4 mounted on a stage 6, and adapted to inspect a workpiece 8 mounted on the stage 6 using retainers 10. The workpiece 8 may include a semiconductor wafer having a notch or other locating feature by which the workpiece 8 may be repeatably located on the stage 6. The microscope 4 includes an objective 12 with a lens 14 movably mounted to a horizontal support arm 16 by a vertical member 18 for vertical movement in the direction of arrow 20. The arm 16 may be adapted for horizontal movement in the direction of arrow 22 via a linear actuator 24 mounted to the stage 6 via a vertical arm 26 and a base 28.

The microscope 4 may further be adapted for horizontal movement relative to the stage 6 in two perpendicular horizontal directions to achieve scanning of the surface of the workpiece 8. The microscope 4 may thus view a portion of the workpiece 8 in an optical path 30. Although the system 2 is illustrated as having a microscope 4 moveable with respect to a fixed stage 6, it will be appreciated that the invention finds application in systems having a stage 6 moveable with respect to a fixed microscope 4, as well as other systems having relative motion between the state 6 and the microscope 4.

The system 2 further includes an optical indicia device 40 mounted to the stage 6 via a base 42, a vertical arm 44 extending upward from the base 42 and supporting a sleeve 46 with a horizontal attachment arm 48 extending outwardly therefrom and supportably engaging the device 40 in the optical path 30. The optical indicia device 40 may thus be supported in a horizontal plane generally parallel with that of the workpiece 8 in the path 30, and spaced from the workpiece 8 by a distance 48 between the workpiece 8 and the microscope 4. The mounting apparatus 42, 44, 46, and 48 may further be adapted to allow movement of the device 40 vertically in the direction of arrow 50.

Figure 2A:
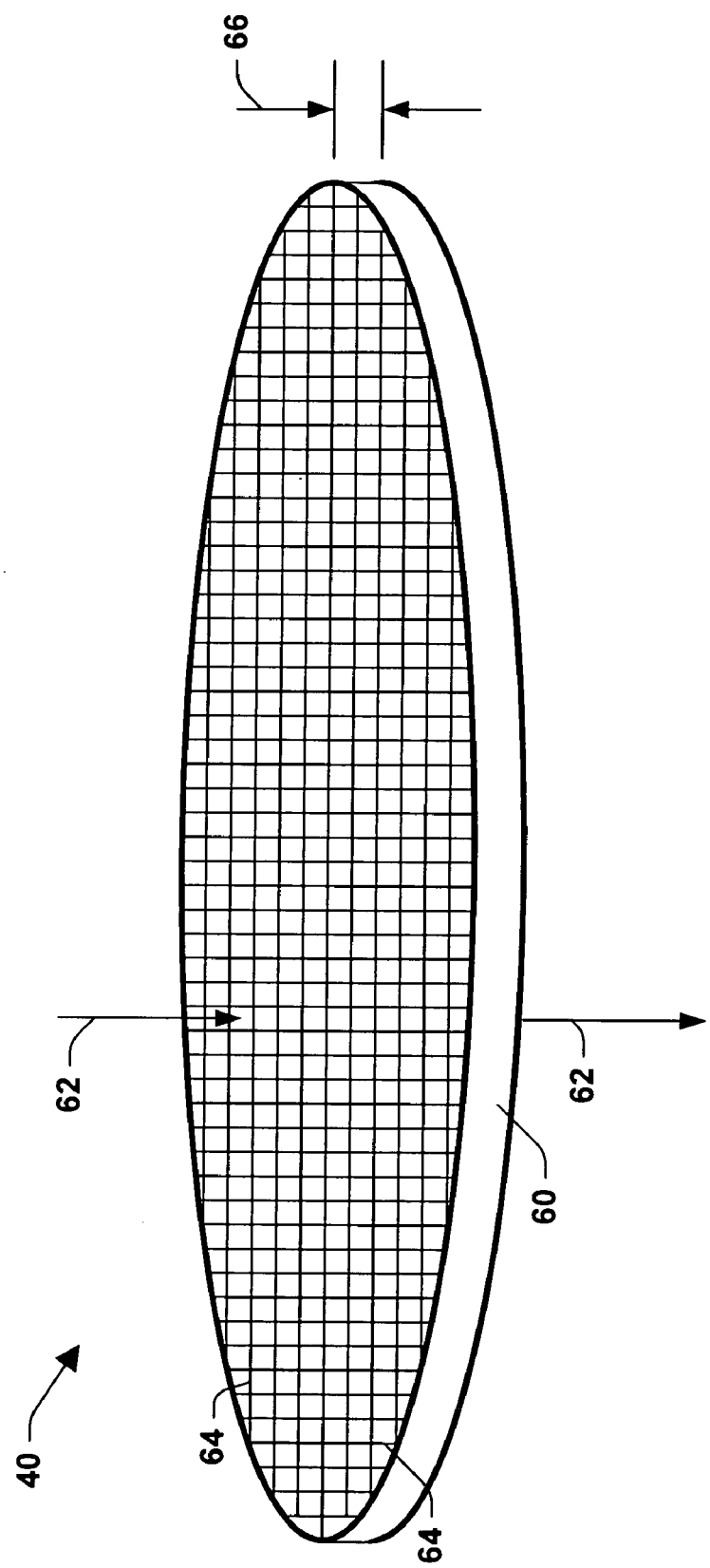
FIG. 2A is a perspective view illustrating an exemplary optical indicia device according to the invention.

Referring also to FIG. 2A, the optical indicia device 40 may comprise a transparent member 60 through which light 62 may travel, which includes non-transparent optical indicia 64 thereon, defining a plurality of transparent regions or fields in the device 40. The transparent member 60 may be a low aspect ratio cylinder shape, having a thickness or height 66 as illustrated herein, although other shapes and configurations are deemed to fall within the scope of the invention. The optical indicia 64 may be arranged in a pattern, whereby the transparent regions in the device 40 may have one or more shapes associated therewith. When located in the optical path 30 of the system 2, for example, the transparent regions in the device 40 provide a coordinate system or spacial reference for viewing and locating specific features on the workpiece 8, such as defects. The non-transparent optical indicia (e.g., lines) in the device 40 may be further employed to provide a segmented view of a blank workpiece 8, to facilitate quick location of surface defects via field comparison techniques.

Figure 2B:
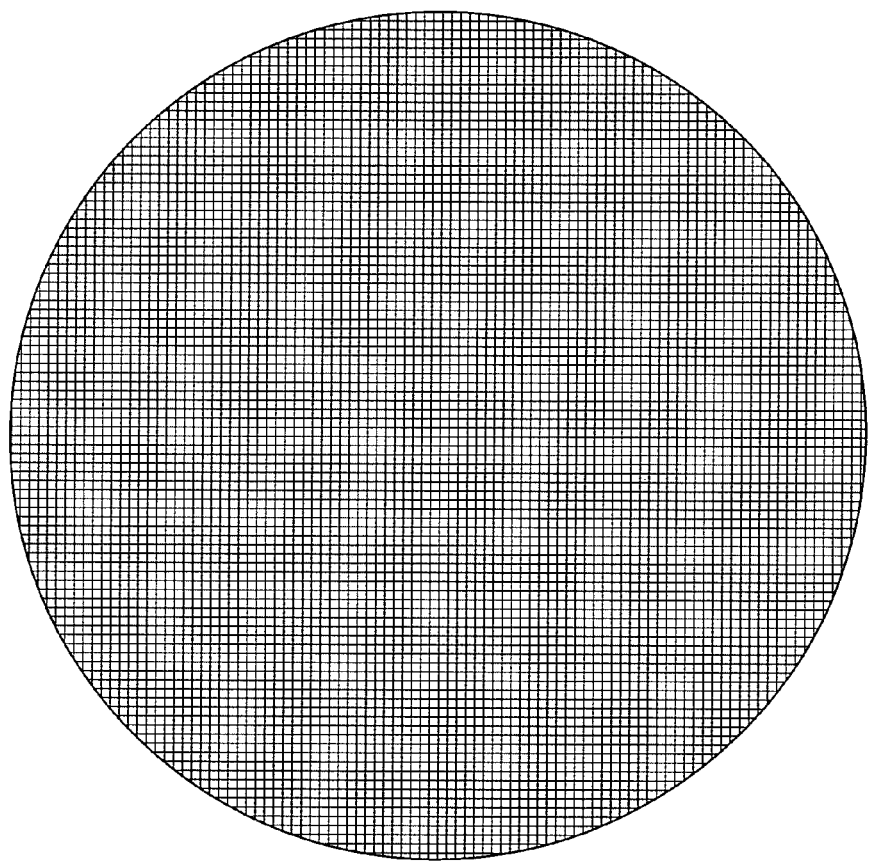
FIGS. 2B through 2E are top plan views illustrating various exemplary optical indicia devices in accordance with the present invention.
Figure 2C:
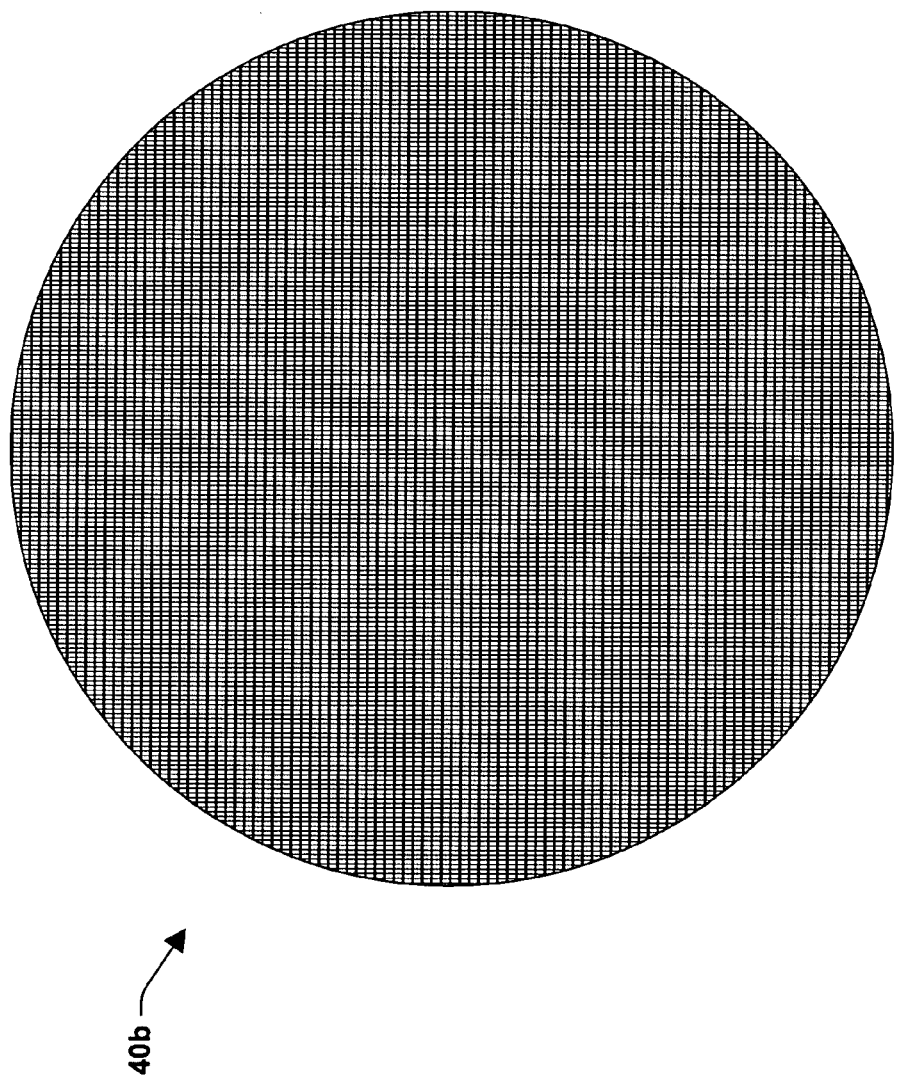

Referring also to FIGS. 2B through 2E, several exemplary optical indicia devices 40a, 40b, 40c, and 40d, respectively, are illustrated. The invention contemplates many different optical indicia patterns and associated transparent region shapes, some of which are illustrated in the figures. For example, the device 40a of FIG. 2B illustrates a two dimensional grid patterns of indicia creating a plurality of rectangular shaped transparent regions through which light may pass. The optical indicia patterns may be provided in various indicia spacings, as illustrated in the device 40b of FIG. 2C, wherein a finer grain rectangular shape pattern is achieved. This may be employed, for example, to provide a higher resolution determination of the location of identified defects.

Figure 2D:
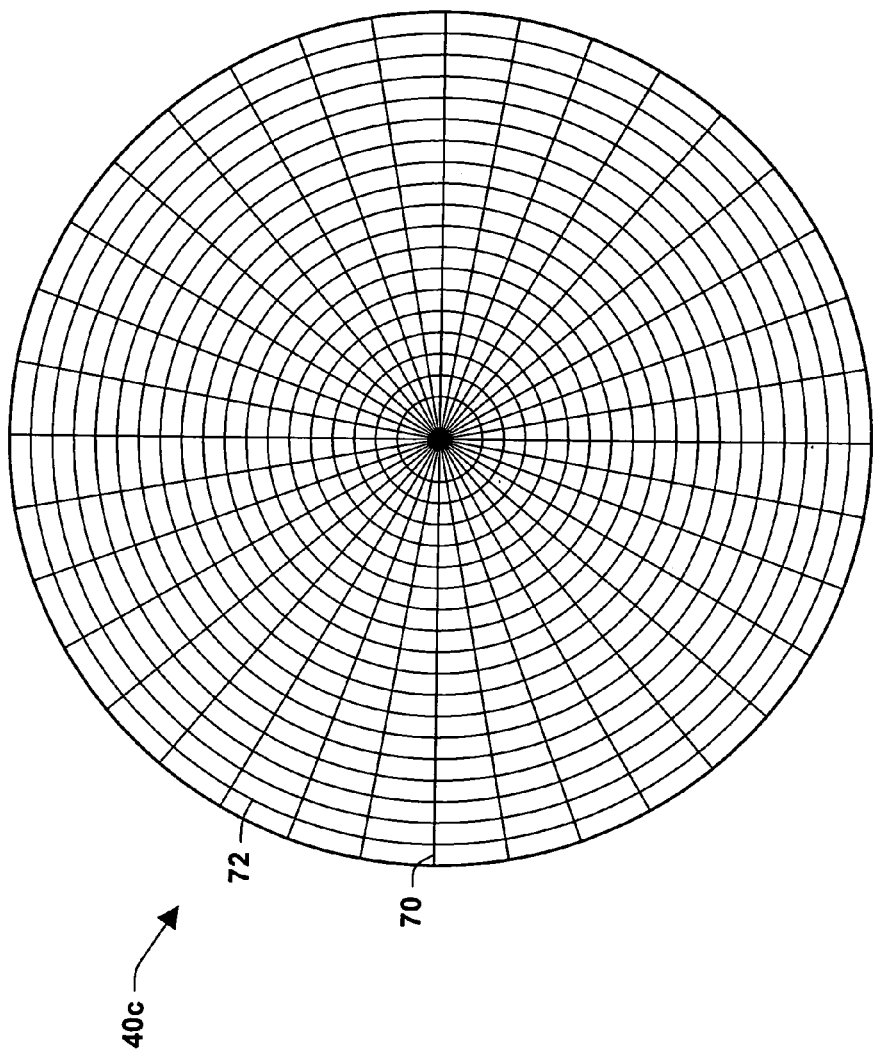
Figure 2E:
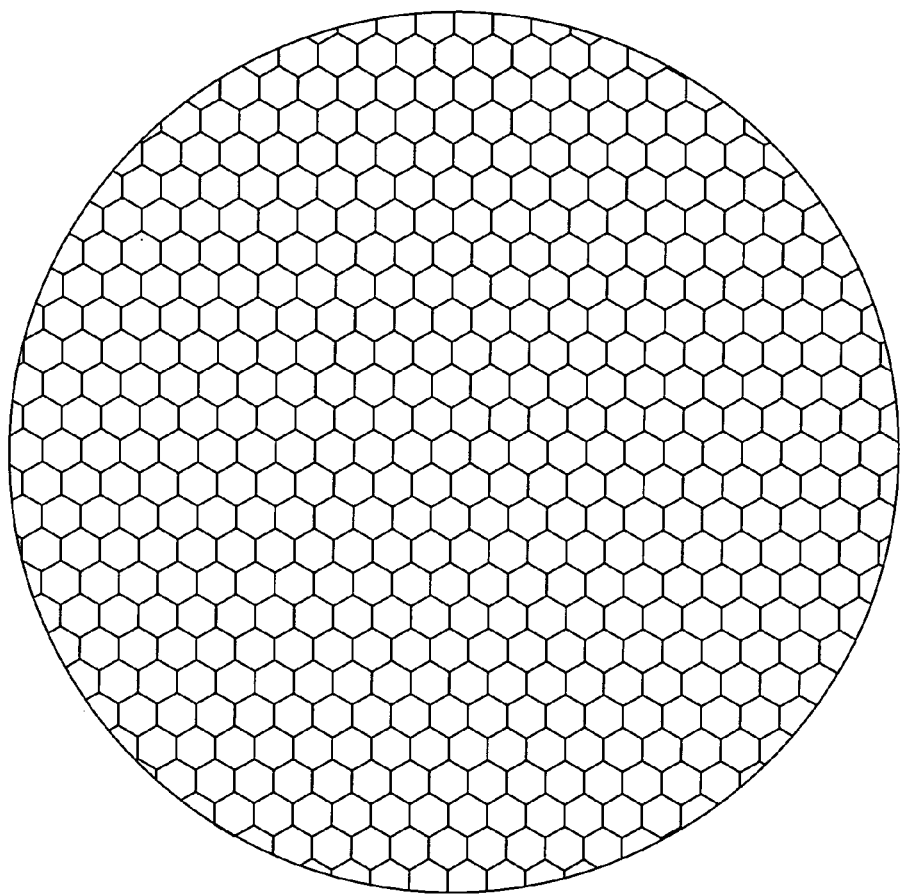

In FIG. 2D, another optical indicia pattern is illustrated in the device 40c, wherein non-transparent radial lines 70 and circumferentially disposed curvilinear lines 72 provide a segmentation pattern wherein the transparent shapes defined thereby are non-uniform. It will be further appreciated that the device 40c provides a polar coordinate system whereas the device 40a of FIG. 2B provides a Cartesian coordinate system. Referring also to FIG. 2E, another exemplary pattern is illustrated in an optical indicia device 10d, having linear non-transparent indicia arranged to form a plurality of hexagonally shaped transparent regions. It will be appreciated that while various exemplary patterns and arrangements are illustrated and described herein, that many other patterns and shapes are possible and are contemplated as falling within the scope of the present invention.

Figure 3:
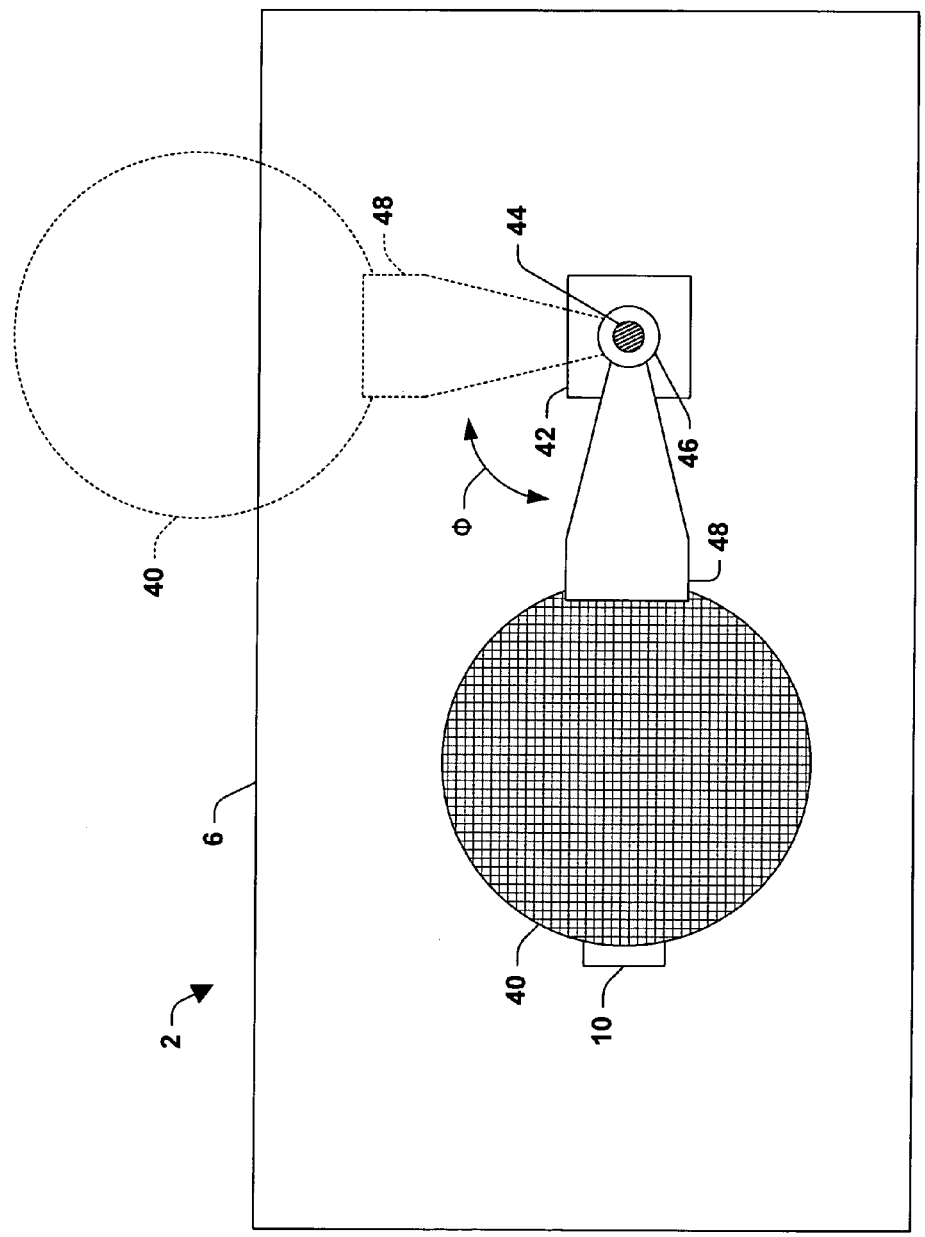
FIG. 3 is a plan view of a portion of the system of FIG. 1, taken along line 3—3 of FIG. 1, illustrating other aspects of the invention.

Referring now to FIG. 3, a top view of a portion of the system 2 is illustrated, taken along line 3—3 of FIG. 1, wherein the sleeve 46 is mounted around the vertical arm 44 to allow pivotal movement of the optical indicia device 40 and the associated horizontal attachment arm 48 through an angle ϕ about the axis of the arm 44. This pivotal movement allows the device 40 to be easily moved into and out of the optical path 30 between the workpiece 8 and the microscope 4. Detents (not shown) may be provided in the pivotal mounting of sleeve 46 and arm 44 to provide repeatable angular location of the device 40 in and/or out of the optical path 30. For example, one detent position may locate the device 40 directly above the workpiece 8, and another detent position may locate the device 40 completely out of the optical path 30.

This angular repositioning of the device 40 is useful, for example, where a user is examining a patterned workpiece using field comparison techniques, whereby two or more optically discernable fields in the wafer pattern are compared to determine if a defect is likely in any one field. In this situation the optical indicia device 40 may be swung out of the optical path to the position indicated in dashed lines in FIG. 3. Once a defect (or potential defect) has been identified in the workpiece, the device 40 may be rotated into position in the optical path 30 to allow location of the defect using the grid or other pattern on the device 40. In this regard, the optical indicia 64 on the device 40 may provide location information regarding the relative position of the microscope 4 and the workpiece 8.

In another application of the invention, the optical indicia device 40 may be located in the optical path 30 to provide a grid of discernable fields to facilitate fast defect identification and location for a blank workpiece. The fields or regions provided by the optical indicia device 40 allow field comparison techniques to be employed in identifying blank wafer defects, for example, when a photoresist has been deposited on a wafer, but no patterning has been performed. In this way, the device 40 facilitates defect inspection at different stages of a multi-step manufacturing process, and provides for differentiation between defects occurring at different steps, as illustrated and described in greater detail infra.

Figure 4:
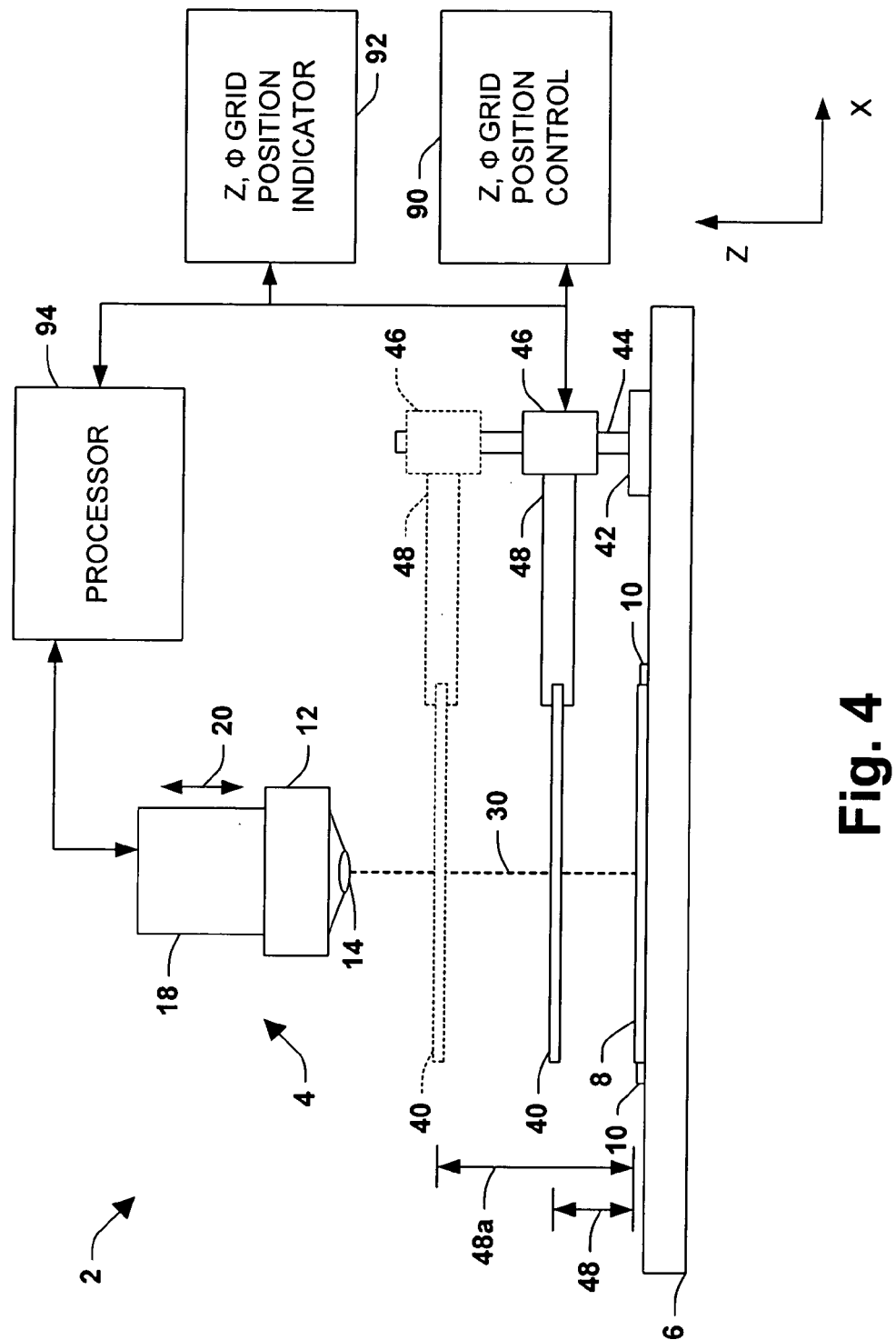
FIG. 4 is a side elevation view of another exemplary optical indicia device having position control and indication features according to another aspect of the invention.

Referring now to FIG. 4, the device 40 may also be moveable in the Z axis direction between a first vertical position (illustrated in solid lines) spaced from the workpiece 8 by a first distance 48, and a second vertical position (illustrated in dashed lines) spaced from the workpiece 8 by a second vertical distance 48a. Detents (not shown) may be provided in the vertically reciprocating interengagement of sleeve 46 and arm 44 to provide repeatable vertical location of the device 40 between the workpiece 8 and the microscope 4 along the optical path 30. This vertical repositioning of the device 40 with respect to the workpiece 8 provides for coarse and fine location information using a single optical indicia device 40, whereby the resolution of the location information may be increased as the device 40 is moved closer to the workpiece 8.

Position controls 90 and position indicators 92 may be provided in the system 2 to control and monitor the position of the optical indicia device 40 in the vertical (Z axis) direction as well as the rotational position ϕ. The controls 90 and indicator 92 may advantageously be connected to communicate with a processor 94, which may further be connected to the microscope 4 and the controls associated therewith (not shown). The system 2 may thus be fully automated, whereby the processor 94 may control the scanning position (e.g., horizontal X and Y axis) of the microscope 4 as well as the position (e.g., vertical Z axis and/or angular rotation position ϕ) of the optical indicia device 40. The processor 94 may further include memory (not shown) in which location or position information relating to the relative position between the microscope 4 and the workpiece (or the device 40) may be stored.

Figure 5:
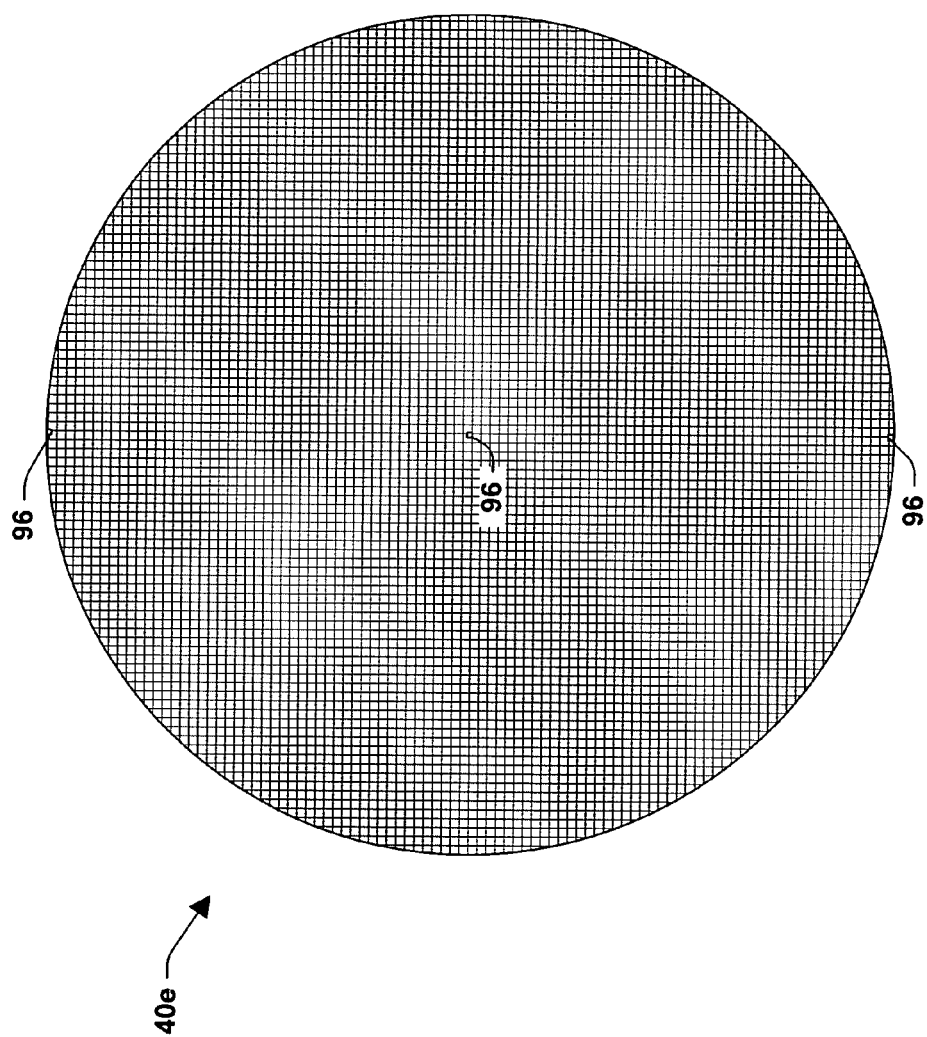
FIG. 5 is a top plan view of another exemplary optical indicia device with fiducial reference indicators in accordance with the invention.

With the device 40 positioned in the optical path, location information may be obtained in one of several manners. For example, the microscope 4 may scan in the X and Y directions (e.g., in a raster pattern) to locate a fiducial or other reference point on the optical indicia device. Referring to FIG. 5, another exemplary optical indicia device 40e is illustrated having non-transparent fiducials 96 located at various points on the device 40e. The processor 94 may be programmed to locate one or more such fiducials 96 by scanning the microscope 4 across the device 40e. When a fiducial 96 is identified by the microscope, subsequent scanning may include recording the number of non-transparent optical indicia (e.g., lines) crossed in the X and Y directions, thereby providing an indication of the relative position of the microscope to the fiducial reference points 96. It will be further appreciated that the processor 94 may further record and account for the vertical (e.g., Z axis) distance (e.g., distance 48) between the device 40 and the workpiece 8 in determining the location of a particular feature.

With the device 40 located in the optical path 30, therefore, the processor 94 may compute location information for any identified feature (e.g., defect) in the workpiece 8. The system 2 may thus identify defects using any scanning technique, and determine the location thereof using the optical indicia device 40. For example, where a patterned workpiece 8 is scanned via moving the microscope 4 in the X and Y directions, a defect may be identified (e.g., using field comparison techniques). The optical indicia device 40 may then be located in the optical path 30, after which the microscope may further scan to locate one or more of the fiducials 96 on the device 40. The processor may determine and count the number of optical indicia encountered in scanning the microscope from the identified defect to the fiducial, whereby the relative location thereof may be determined.

In addition, where a blank wafer or workpiece 8 is being inspected for defects, the optical indicia device 40 may also be advantageously located in the optical path 30 to provide optically discernable fields by which field comparison techniques may be employed to identify defects. In this case, the processor 94 may be programmed to locate a fiducial 96 (e.g., by scanning the microscope 4 in the X and/or Y directions), and then to scan the workpiece 8 for defects, while recording the number of optical indicia encountered during scanning. Once a defect (or likely defect) is identified, the processor can compute the location thereof relative to the fiducial 96, and can further store this location in memory.

Continuing in this fashion, the defects in a blank workpiece 8 may be mapped and stored in memory for subsequent use by the system 2. Thereafter, a patterned workpiece may be inspected for defects (e.g., with the device 40 located out of the optical path 30). Once a defect is identified in the patterned workpiece, the device 40 may be swung into the optical path 30, and the microscope may be scanned to locate a fiducial 96, whereby the relative location of the patterned workpiece defect may be determined. This location may be compared with the blank workpiece defect locations in order to determine whether the defect was caused by an initial processing step (e.g., photoresist deposition) or by an intervening step (e.g., patterning the workpiece). For example, the comparison may include comparing the patterned workpiece defect location with specific blank workpiece defects where the blank workpiece defects are known or believed to be locationally repeatable.

In addition, the patterned workpiece defect locations may be compared to one or more regions (e.g., radially disposed regions in the wafer) where the blank workpiece defects are known or believed to be regionally repeatable. For example, it may be known that defects in a photoresist deposition processing step occur frequently at a distance 100 to 120 mm from the center of a 300 mm diameter wafer. In this example, a patterned workpiece defect occurring in the region may be determined to be caused in the photoresist deposition step as opposed to a subsequent processing step (e.g., patterning step). In this regard, one or more test wafers may be processed according to a photoresist deposition step, and the defects therein may be mapped to determine a regionally repeatable defect distribution. Thereafter, the same (or other) wafers may be processed further (e.g., via patterning) and inspected. The defects therein may be correlated with the regionally repeatable defect distribution identified in the test wafers. Based on the correlation, a determination may then be made as to the process step most likely to have caused the patterned wafer defects.

Figure 6:
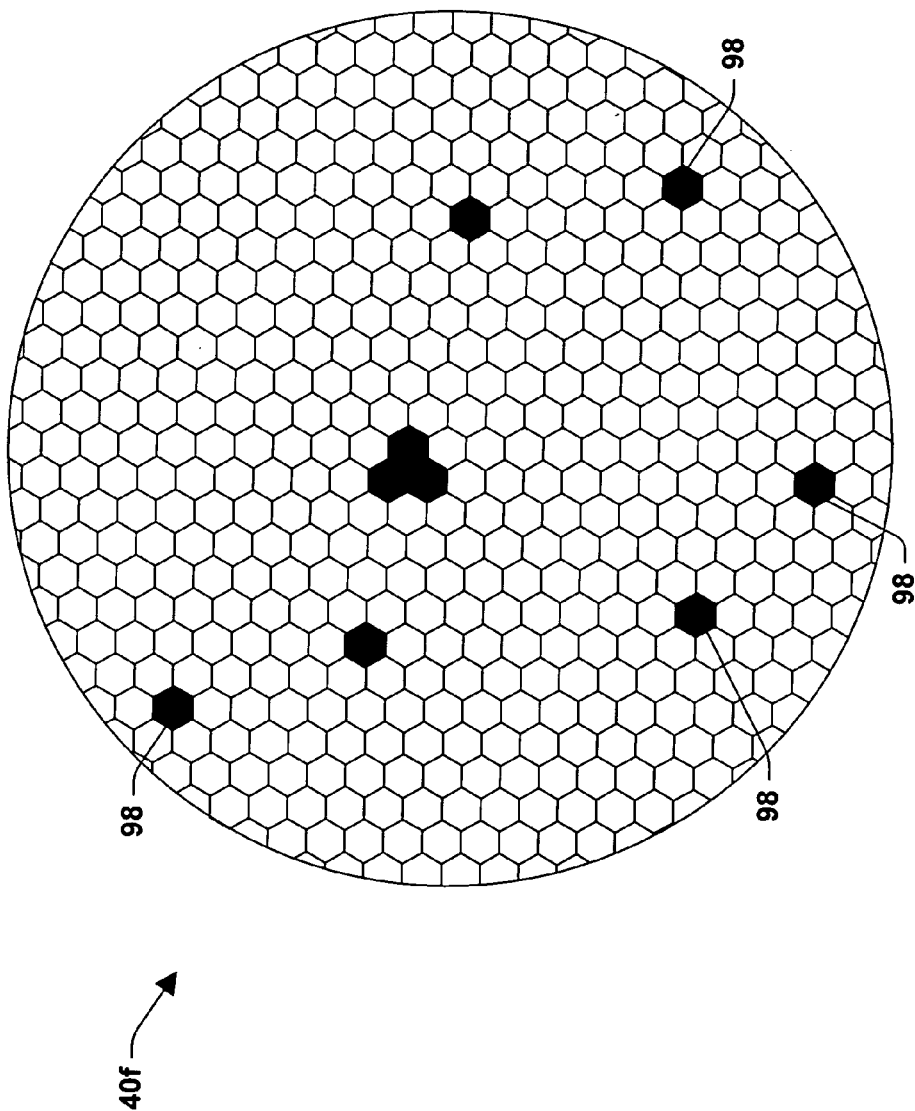
FIG. 6 is a top plan view of another exemplary optical indicia device with defect indicators in accordance with the invention.

In another application of the invention, the optical indicia device 40 may be used to provide an optical mapping of a defect pattern. For example, where a blank workpiece 8 has been inspected or scanned for defects using the microscope 4, the device 40 may be marked with a defect indicator, for later use in overlaying a patterned or other workpiece. Referring now to FIG. 6, another exemplary optical indicia device 40f is illustrated having several optical (e.g., non-transparent) defect indicators 98. In this regard, the system 2 may include a marking apparatus (not shown) adapted to mark a location on a device 40 according to a user command, or under control of the processor 94. For example, the defect indicators 98 may be marked on the device 40f by a controlled light source adapted to expose one or more regions in the optical indicia pattern of the device 40f upon identification of a defect. The device 40f may include, for example, a photo sensitive material (not shown) which will become non-transparent upon exposure to light via the controlled light source, whereby the processor may mark a region or field in the device 40f corresponding to a defect identified in a workpiece 8. The system 2 may be further adapted to include an optical indicia device marking station (not shown), whereat marking apparatus may mark a device 40 according to defect information stored in memory.

The device 40f of FIG. 6 may be employed in discriminating between defects existing in a blank workpiece and those existing in a subsequently patterned workpiece. For example, the defect indicators 98 on the device 40f may represent defects found in a blank semiconductor wafer (e.g., caused by an initial photoresist deposition processing step). Where a patterned wafer is later inspected, the device 40f may be quickly rotated into the optical path 30 above the patterned workpiece, whereby an operator may quickly determine whether the defect location has been previously marked on the device 40f. If so, the user may decide that the defect was not caused in the intervening patterning step, but was instead caused by the photoresist deposition step. Otherwise, the user will determine that the defect was not present in the blank wafer, and may therefore conclude that the defect was caused in such an intervening processing step. The device 40 therefore finds many applications in identifying and locating defects in a workpiece, as well as in aiding in the determination of the cause of such defects in a multi-step manufacturing process.

Figure 7:
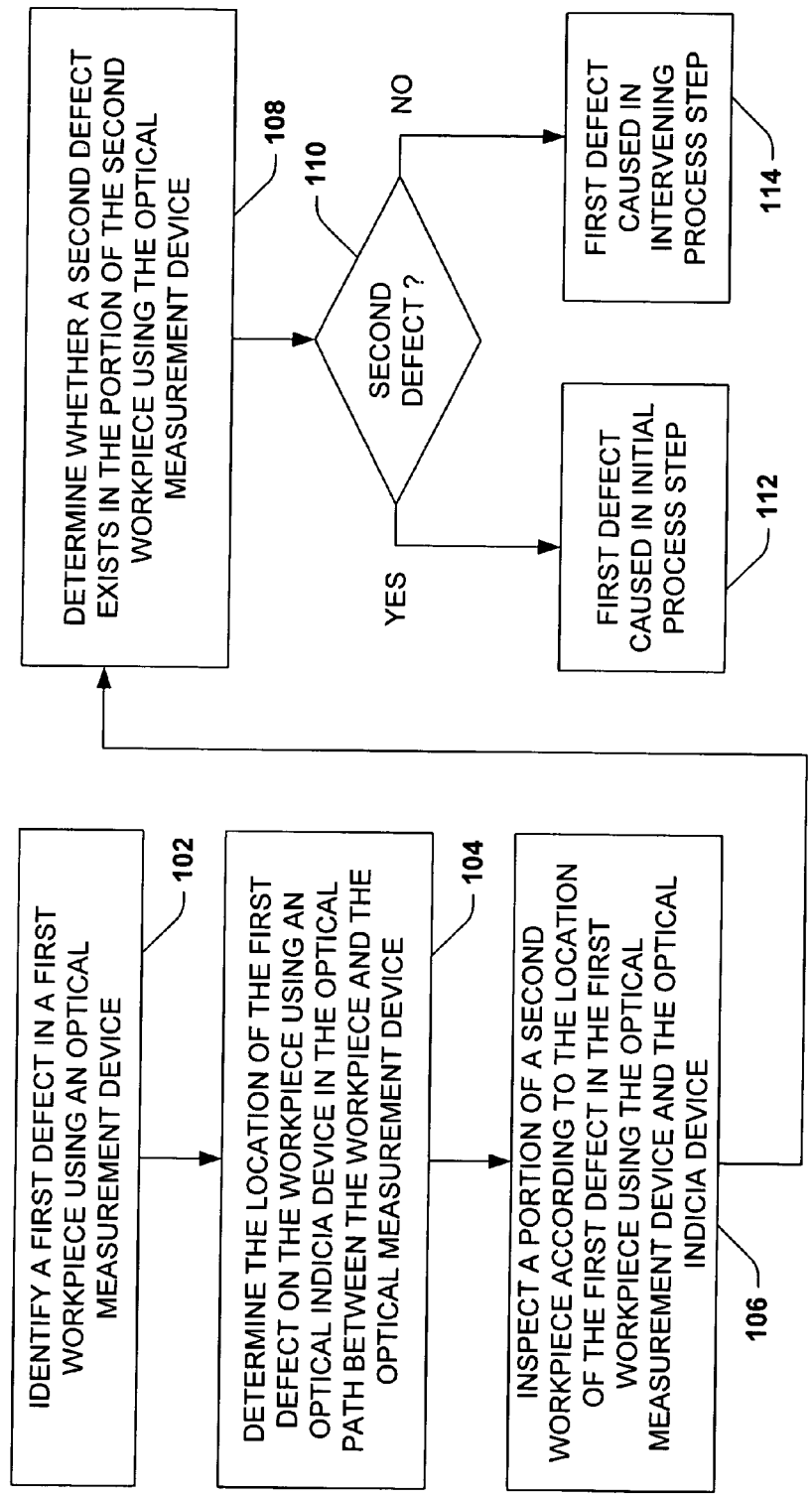
FIG. 7 is a flow diagram illustrating an exemplary method of identifying and locating defects in a workpiece according to yet another aspect of the invention.

Referring now to FIG. 7, an exemplary method 100 of identifying and locating defects in a workpiece is illustrated, wherein a first defect is identified in a first workpiece at step 102 using an optical measurement device (e.g., microscope 4 of system 2). For example, the first workpiece may be a patterned semiconductor wafer. Thereafter the location of the first defect is determined at step 104 using an optical indicia device (e.g., device 40) in the optical path (e.g., path 30) between the workpiece and the optical measurement device. For example, the optical indicia device 40 may be rotated from the dashed line position of FIG. 3 into the optical path 30. A portion of a second workpiece (e.g., a blank or unpatterned semiconductor wafer) may then be inspected at step 106 according to the location of the first defect in the first workpiece. For example, the first and second workpieces may have been processed through a photoresist deposition step, and the first workpiece may have been further processed according to a patterning step.

The portion of the second workpiece inspected at step 106 may, for example, be the same location as that of the first defect in the first workpiece, such as where it is known or believed that defects occurring prior to the patterning step are locationally repeatable. The portion of the second workpiece inspected at step 106 may further be a region related to the location of the first defect (e.g., a range or band radially spaced from the center of the workpiece) where it is believed or known that defects occurring in the photoresist deposition step are regionally repeatable. At steps 108 and 110, a determination is made as to whether a second defect exists in the portion of the second workpiece. If so, a determination may be made at step 112 that the first defect (e.g., in the patterned wafer) was caused in an initial process step (e.g., photoresist deposition). If not, a determination may be made at step 114 that the first defect was caused in an intervening process step (e.g., during patterning). The method thus provides defect location mapping as well as a determination of the probable cause of defects via the optical indicia device.

Figure 8:
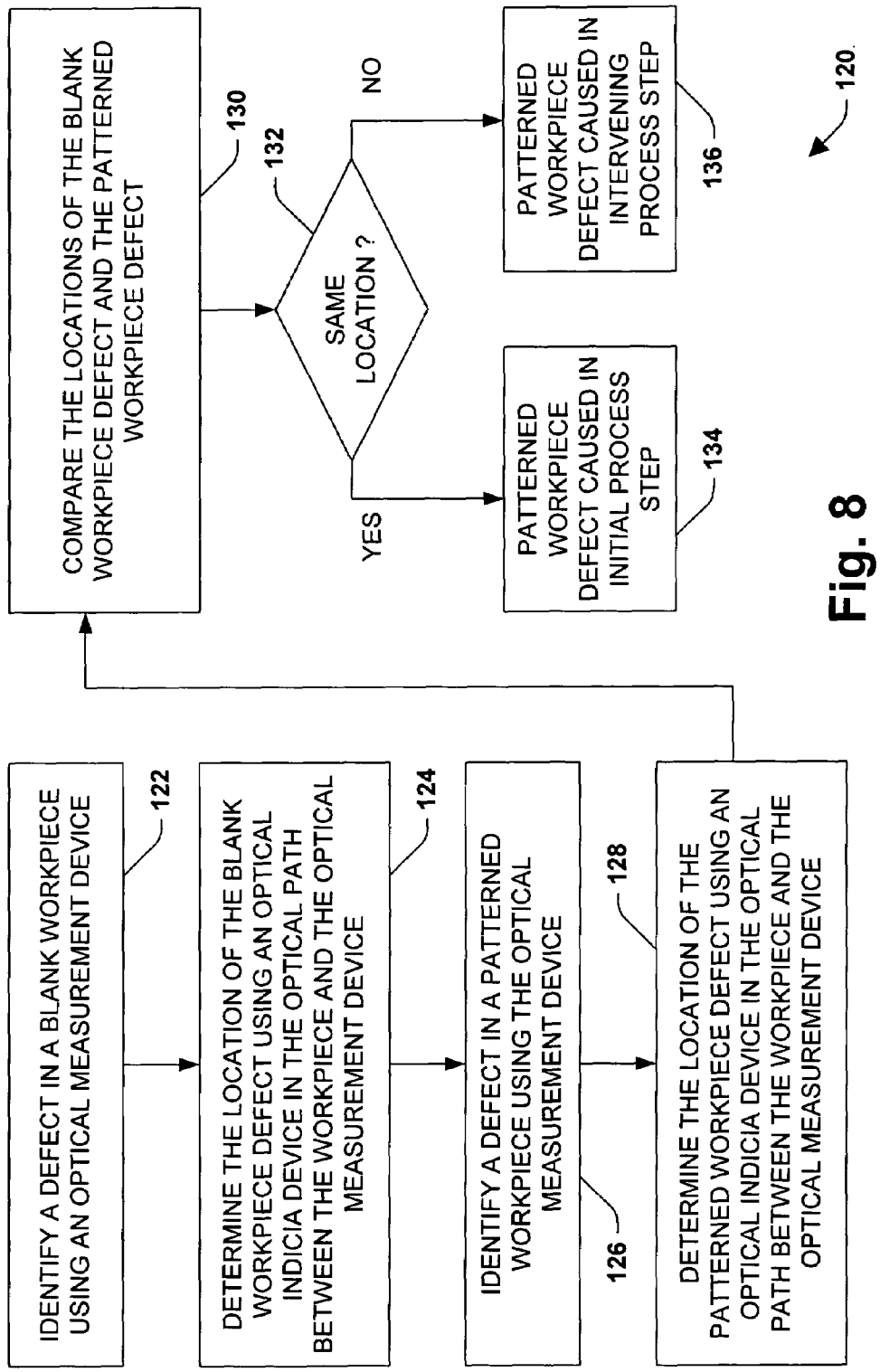
FIG. 8 is a flow diagram illustrating another exemplary method of identifying and locating defects in a workpiece according to the invention.

Referring now to FIG. 8, another exemplary method 120 is illustrated for identifying and locating defects in a workpiece. Beginning at step 122, a defect is identified in a blank workpiece using an optical measurement device. Step 122 may include field comparison techniques in conjunction with an optical indicia device, such as device 40. At step 124, the location of the blank workpiece defect identified at step 122 is determined using an optical indicia device in the optical path between the workpiece and the optical measurement device. Thereafter, a defect is identified in a patterned workpiece using the optical measurement device at step 126, and the location thereof is determined at step 128 using the optical indicia device. A comparison is then made at steps 130 and 132 of the locations of the blank and patterned workpiece defects. Where the locations are the same, a determination may be made at step 134 that the patterned workpiece defect was caused in an initial step. Where the locations are not the same, a determination may be made at step 136 that the patterned workpiece defect was caused in an intervening process step.

Referring now to FIG. 9, an exemplary method 150 of identifying a defect in a blank workpiece is illustrated in accordance with another aspect of the invention. Beginning at step 152, the images of two portions or fields of a blank workpiece are viewed through two transparent regions in an optical indicia device, using an optical measurement device. The two images are then compared at step 154, after which decision step 156 determines if the images are different. If not, it may be determined at step 158 that no defect exists. If, however, the images differ, further inspection may be made to identify a defect in one of the two workpiece portions at step 160 using the optical measurement device. In this manner, the optical indicia device may be advantageously employed to facilitate field comparison techniques in identifying defects in a blank workpiece.

Although the invention has been shown and described with respect to one or more implementations, equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the term "includes" is used in either the detailed description and the claims, such term is intended to be inclusive in a manner similar to the term "comprising."

What is claimed is:

1. An optical defect inspection system for identifying and locating defects in a workpiece, comprising:
   an optical measurement device adapted to view the workpiece along an optical path; and
   an optical indicia device located in the optical path, adapted to provide location information with respect to a defect in the workpiece;
   wherein the optical indicia device comprises a generally planar transparent member having non-transparent optical indicia defining a plurality of transparent regions in the optical indicia device along the optical path, wherein the optical indicia device is mounted in a first plane generally perpendicular to the optical path, and wherein the transparent member is movable with respect to the workpiece between a first position in the first plane, and a second position in a second plane, and wherein the second plane is parallel with the first plane.

2. The system of claim 1, wherein the first and second planes are generally horizontal and wherein the optical path is generally vertical.

3. The system of claim 1, wherein the transparent member is generally laterally movable with respect to the optical path.

4. The system of claim 1, wherein the optical indicia device is movable between a first position wherein at least a portion of the optical indicia device is located in the optical path, and a second position wherein the optical indicia device is located outside the optical path.

5. An optical defect inspection system for identifying and locating defects in a workpiece, comprising:
   an optical measurement device adapted to view the workpiece along an optical path; and
   an optical indicia device located in the optical path, adapted to provide location information with respect to a defect in the workpiece;
   wherein the optical indicia device comprises a generally planar transparent member having non-transparent optical indicia defining a plurality of transparent regions in the optical indicia device along the optical path, wherein the optical indicia device is mounted in a first plane generally perpendicular to the optical path, and wherein the optical indicia device is movable between a first position wherein the optical indicia device is located in the optical path, and a second position wherein the optical indicia device is located outside the optical path.

6. In an optical defect inspection system having an optical measurement device adapted to view a workpiece along an optical path and an optical indicia device located in the optical path between the workpiece and the optical measurement device, a method of identifying and locating defects in the workpiece, comprising:
   identifying a first defect in a first workpiece using the optical measurement device;
   determining a location of the first defect using the optical indicia device;
   inspecting at least a portion of a second workpiece using the optical measurement device and the optical indicia device according to the location of the first defect in the first workpiece;
   determining whether a second defect exists in the inspected portion of the second workpiece using the optical measurement device; and
   correlating the first and second defects according to the location of the first defect in the first workpiece, if a second defect exists in the inspected portion of the second workpiece.

7. The method of claim 6, wherein determining the location of the first defect using the optical indicia device comprises obtaining location information from the optical indicia device regarding the relative position of the optical measurement device and the first workpiece.

8. The method of claim 7, wherein the optical indicia device comprises a transparent member having non-transparent optical indicia defining a plurality of transparent regions in the transparent member, wherein at least one of the transparent regions is located along the optical path, and wherein the optical indicia device is adapted to provide the location information according to the at least one transparent region located along the optical path.

9. The method of claim 8, wherein inspecting the portion of a second workpiece using the optical measurement device and the optical indicia device according to the location of the first defect in the first workpiece comprises locating the optical measurement device with respect to the second workpiece via the optical indicia device to view the second workpiece through the at least one transparent region located along the optical path.

10. The method of claim 6, wherein correlating the first and second defect according to the location of the first defect in the first workpiece comprises determining whether the cause of the second defect is also the cause of the first defect.

11. In an optical defect inspection system having an optical measurement device adapted to view a workpiece along an optical path and an optical indicia device located in the optical path between the workpiece and the optical measurement device, a method of identifying and locating defects in the workpiece, comprising:
   identifying a blank workpiece defect in a blank workpiece using the optical measurement device;
   determining a location of the blank workpiece defect using the optical indicia device;
   identifying a patterned workpiece defect in a patterned workpiece using the optical measurement device;
   determining a location of the patterned workpiece defect using the optical indicia device; and
   correlating the locations of the blank workpiece defect and the patterned workpiece defect in order to determine a cause of the patterned workpiece defect.

12. In an optical defect inspection system having an optical measurement device adapted to view a workpiece along an optical path and an optical indicia device located in the optical path between the workpiece and the optical measurement device and having a transparent member with non-transparent optical indicia defining a plurality of transparent regions in the optical indicia device along the optical path, a method of identifying a defect in a blank workpiece, comprising:
   viewing images of two portions of the workpiece through two of the transparent regions using the optical measurement device;
   comparing the images of the two portions of the workpiece; and
   identifying a defect in the workpiece in one of the two portions of the workpiece if there is a difference in the images of the two portions of the workpiece.

13. An optical defect inspection system for locating defects in a workpiece, comprising:
   viewing means for viewing at least a portion of a workpiece along an optical path; and
   defect location means for locating a defect in the workpiece;
   wherein the defect location means is selectively movable between a first position in the optical path between the viewing means and the workpiece, and a second position outside the optical path, and wherein the defect location means is adapted to provide location information relating to the relative position of the defect with respect to the workpiece.

* * * * *